United States Patent [19]

Djuric et al.

[11] Patent Number: 4,754,055
[45] Date of Patent: Jun. 28, 1988

[54] ALLENIC PROSTACYCLINS

[75] Inventors: Stevan W. Djuric, Evanston; Masateru Miyano, Northbrook, both of Ill.

[73] Assignee: G. D. Searle & Co., Chicago, Ill.

[21] Appl. No.: 905,908

[22] Filed: Sep. 10, 1986

Related U.S. Application Data

[63] Continuation-in-part of Ser. No. 713,116, Mar. 18, 1985, abandoned.

[51] Int. Cl.[4] ............................................. C07C 177/00
[52] U.S. Cl. .................................... 560/116; 560/119; 560/10; 502/431; 502/498; 502/501
[58] Field of Search ......................... 560/119, 116, 10; 502/431, 498, 501

[56] References Cited

U.S. PATENT DOCUMENTS 4,578,505  3/1986  Collins ................................ 560/118

FOREIGN PATENT DOCUMENTS 202840  10/1985  Japan ................................... 560/118

Primary Examiner—Robert Gerstl
Attorney, Agent, or Firm—J. Timothy Keane; R. E. L. Henderson; Paul D. Matukaitis

[57]  ABSTRACT

The present invention describes allenic prostacyclin derivatives of the formula:

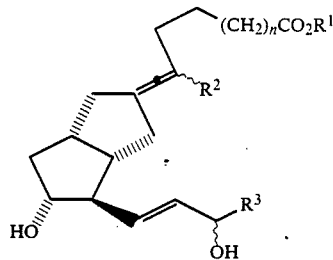

wherein:
n is 0, 1, or 2;
$R^1$ is hydrogen, lower alkyl, or a pharmaceutically acceptable cation;
$R^2$ is hydrogen, lower alkyl, cycloalkyl, heteroaryl, halogen, phenyl, alkylthio, phenylthio, alkylsulfinyl, phenylsulfinyl or trifluoromethyl;
$R^3$ is lower alkyl, cycloalkyl, phenyl, benzyl, cycloheteroalkyl, lower alkyl having one to eight carbons substituted with one or more fluorines or containing 1 or 2 unsaturated bonds; and
carbon 15 may be in the R or the S configuration, or a mixture of R and S.

These compounds are useful for the treatment of platelet dysfunction, atherosclerosis, allergic disorders, gastric ulcers, hypertension and tumor cell metastasis. Also disclosed is the process for preparing them and the appropriate intermediates.

9 Claims, 3 Drawing Sheets

CHART A
I ALLENE PROSTACYCLIN
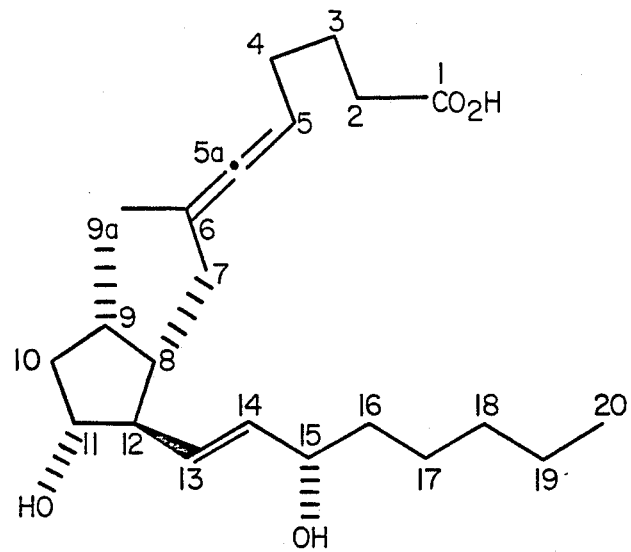
II PROSTANE SKELETON
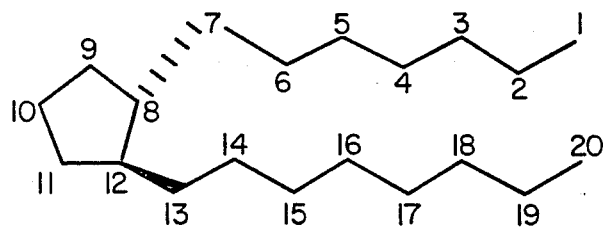
III PROSTACYCLIN (PGI$_2$)
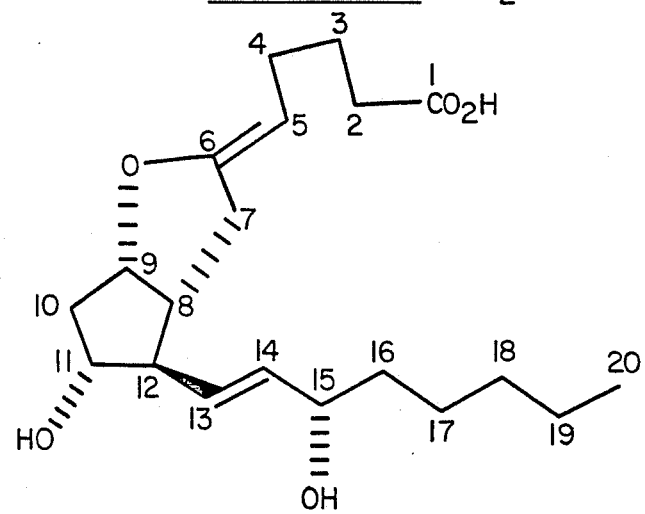

CHART B
SCHEME I
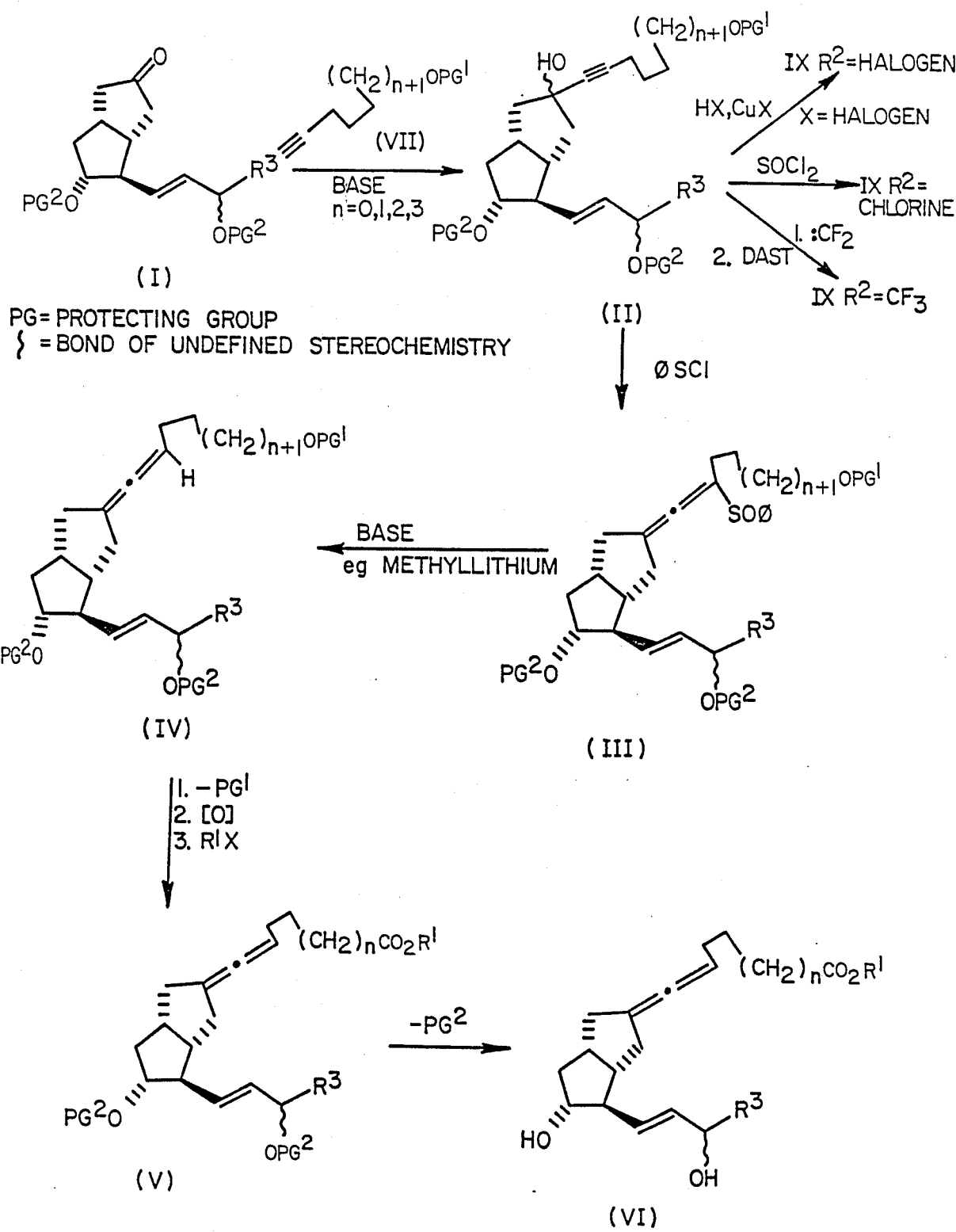

CHART C
SCHEME II
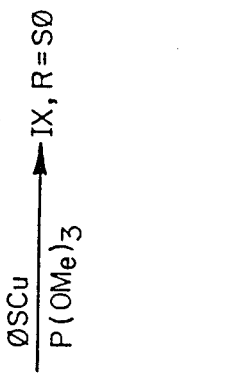
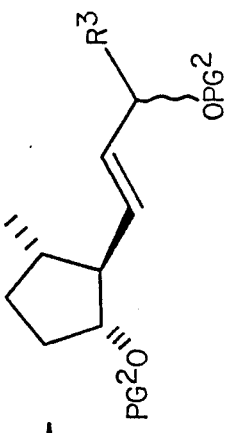
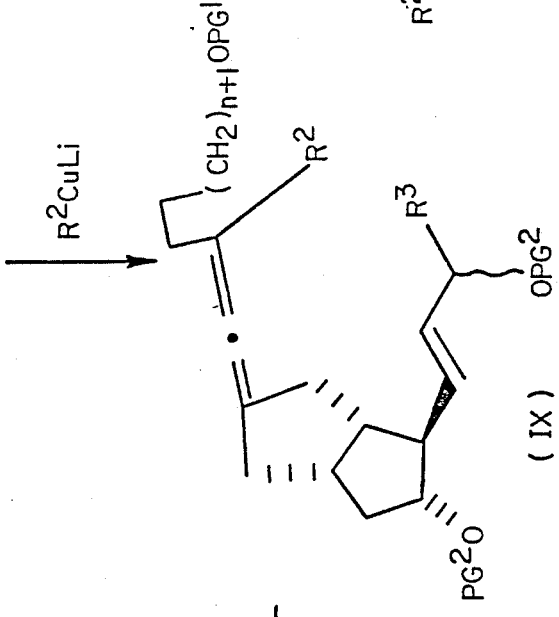
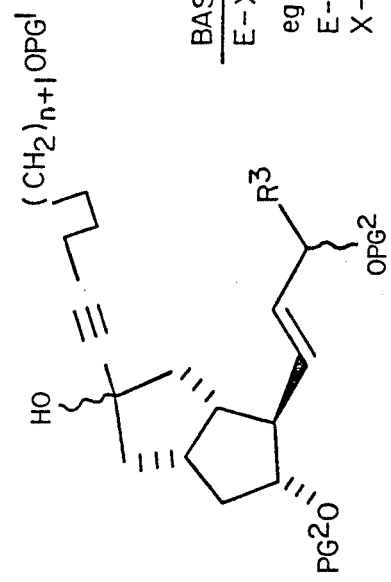
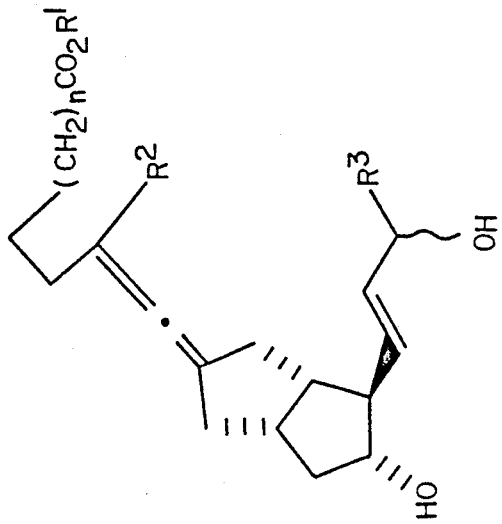
$R^2$ = ALKYL
    = ARYL
    = HETEROARYL

ALLENIC PROSTACYCLINS

BACKGROUND OF THE INVENTION

1. Field of the Invention

This application is a continuation-in-part of application Ser. No. 06/713,116 filed Mar. 18, 1985. now abandoned.

This invention relates to prostacyclin derivatives and to a process for preparing them. More particularly the invention relates to novel prostacyclin ($PGI_2$) derivatives. More particularly, this invention relates to $PGI_2$ derivatives of formula I, Chart A with discloses allenic carbacyclins.

2. Description of Prior Art

The prostaglandins, prostacyclins, carbacyclins, and their analogs are well-known organic compounds derived from prostanoic acid which was the structure and atom numbering shown in figure II chart A.

As drawn hereinafter the formulas represent a particular optically active isomer having the same absolute configuration as $PGI_2$. However, both the R and S configuration at carbon 15 (bearing the hydroxyl group) or mixtures are included within the scope of this invention.

In the formulas, broken line attachments to the cyclopentane ring or side chain indicate substituents in alpha configuration, i.e. below the plane of the cyclopentyl ring or side chain. Heavy solid line attachments indicate substitutents in beta configuration, i.e. above the plane.

For background on prostaglandins, see for example Bergstrom et al., Pharmacol. Rev. 20, 1 (1968). For related compounds see Pace-Asciak et al., Biochem., 10 3657 (1971). Related compounds are described in a publication on 6-keto-prostaglandin $F_{1\alpha}$ by Pace-Asciak, J. Am. Chem. Soc. 2348 (1976) and a publication on "PGX" (6,9$\alpha$-oxido-9$\alpha$,15$\alpha$-dihydroxyprosta(Z)5,(E)13-dienoic acid) by E. J. Corey et al., J. Am. Chem. Soc. 99 20016 (1977).

The potential pharmaceutical value of prostacyclins and prostacyclin analogs is described by S. Moncada. Br. J. Pharmac. (1982), 76, 003–031 and by Honn et al. (U.K.) Biochemical Pharmacology (1983) 32, No. 1, 1-11.

The compounds of this invention may be regarded as analogs of prostacyclin and prostacyclin type compounds.

Prostacyclin, an organic compound related to prostaglandins, is (5Z)-9-deoxy-6,9$\alpha$-epoxy-$\Delta^5$-$PGF_1$. For its synthesis and structure see for example R. A. Johnson et al., J. Am. Chem. Soc. 99, 4182 (1977) and Prostaglandins, 12, 915 (1976), and E. J. Corey et al., cited above. For some of its biological properties uses see the references cited in the Johnson references.

Prostaglandins and prostacyclin-type compounds, including derivatives and analogs, are extremely potent in causing various biological responses. For that reason, these compounds are useful for pharmacological purposes. A few of those biological responses are: inhibition of blood platelet aggregation, stimulation of smooth muscle, inhibition of gastric secretion, inhibition of tumor cell metastasis, and reduction of undesirable gastrointestinal effects from systemic administration of prostaglandin synthetase inhibitors.

Because of these biological responses, prostaglandins and prostacyclin-type compounds are useful to study, prevent, control, or alleviate a wide variety of diseases and undersirable physiological conditions in mammals, including humans, useful domestic animals, pets, and zoological specimens, and in laboratory animals, for example, mice, rats, rabbits, and monkeys.

Prostacyclin and prostacyclin-type compounds are useful whenever it is desired to inhibit platelet aggregation, to reduce the adhesive character of platelets, and to remove or prevent the formation of thrombi or tumor cell metastasis in mammals, including man, rabbits, and rats. For example, these compounds are useful in the treatment and prevention of myocardial infarcts, to treat and prevent postoperative surgery, and to treat conditions such as atherosclerosis, hypertension, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administraton is preferred. Doses in the range about 0.01 to about 10 mg. per kg. of body weight per day are used, the exact dose depending on the age, weight, and condition of the patient or animal, and on the frequency and route of administration.

The addition of prostacyclin and prostacyclin-type compounds to whole blood provides in vitro applications such as storage of whole blood to be used in heart lung machines. Additionally, Whole blood containing these compounds can be circulated through limbs and organs, e.g. heart and kidneys, whether attached to the original body, detached and being preserved or prepared for transplant, or attached to a new body. Blocking of aggregated platelets is avoided by the presence of these compounds. For this purpose, the compound is added gradually or in single or multiple portions to the circulating blood, to the blood of the donor person or animal, to the perfused body portion, attached or detached, to the perfused body portion, attached or detached, to the recipient, or to two or all of those at a whole blood. These compounds are also useful in preparing platelet-rich concentrates from blood for use in treating thrombocytopenia or in chemotherapy.

Prostaglandins E and F and related compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, they are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the later purpose, the compound is administered by intravenous infusion immediately after abortion or delivery at a dose in the range about 0.01 to about 50 $\mu$g. per kg. of body weight per minute until the desired effect is obtained. Subsequent doses are given by intravenous, subcutaneous, or intramuscular injection or infusion during puerperium in the range 0.01 to 2 mg. per kg. of body weight per say, the exact dose depending on the age, weight, and condition of the patient or animal.

Prostaglandins and prostacyclin-type compounds are also useful in mammals, including man and certain useful animals, e.g. dogs and pigs, to reduce and control excessive gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 µg. per kg. of body weight per minute, or in a total daily dose by injection of infusion in the range about 0.01 to about 10 mg. per kg. of body weight per day, the exact dose depending on the age, weight, and condition of the patient or animal, and on the frequency and route of administration.

Prostaglandins and prostacyclin-type compounds and their analogs are also useful in mammals, including man, to treat primary neoplasms and other cancers or tumors by inhibiting the production of metastasis away from the primary lesion. These compounds can be used singularly or in combination with other anti-metastatic treatment such as chemotherapy and radiation therapy. See Honn et al., Biochemical Pharmacology, 32, 1–11 (1983), for mechanisms by which prostacyclins ($PGI_2$) are thought to prevent the metastasis by inhibiting the association of the released tumor cells with platelets and/or the blood vessel wall thereby inhibiting the formation of new metastatic foci away from the primary lesion.

To treat with an anti-metastatic amount of the prostaglandin or prostacyclin type compound, the compound is administered by infusion or injection, intravenously, subcutaneously or intramuscularly in an infusion dose range of about 0.001–50 mg/kg of body weight per minute, or in a total daily dose by injection in the range of about 0.01 to 10 mg/kg of body weight per day, the exact dose depending upon the age, weight and condition of the patient or animal, and on the frequency and route of administration.

Prostaglandins and prostacyclin-type compounds are also useful in reducing the undesirable gastrointestinal effects resulting from systemic administration of anti-inflammatory prostaglandin synthetase inhibitors, and are used for that purpose by concomitant administration of prostaglandins or prostacyclin-type compound and anti-inflammatory prostaglandin synthetase inhibitor. See Partridge et al., U.S. Pat. No. 3,781,429, for a disclosure that the ulcerogenic effect induced by certain non-steroidal and steroidal anti-inflammatory agents in rats is inhibited by concomitant oral administration of certain prostaglandins of the E and A series, including $PGE_1$, $PGE_2$, $PGE_3$, 13,14-dihydro-$PGE_1$, and the corresponding 11-deoxy-PGE and PGA compounds. Prostaglandins and prostacyclin-type compounds are useful, for example, in reducing the undesirable gastrointestinal effects resulting from systemic administration of indomethacin, phenylbutazone, and aspirin. These are substances specifically mentioned in Partridge et al., as non-steroidal, anti-inflammatory agents. These are also known to be prostaglandin synthetase inhibitors.

The anti-inflammatory cyclooxygenase inhibitor, for example indomethacin, aspirin, or phenylbutazone, is administered in any of the ways known in the art to alleviate an inflammatory condition, for example, in any dosage regimen and by any of the known routes of systemic administration.

The prostaglandins or prostacyclin-type compound is administered along with the anti-inflammatory prostaglandin synthetase inhibitor either by the same route of administration or by a different route. For example, if the anti-inflammatory substance is being administered orally, the prostaglandins or prostacyclin-type compound is also administered orally, or alternatively, as administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin or prostacyclin-type compound is also administered rectally. Further, the prostaglandin or prostacyclin derivative can be conveniently administered orally or, in the case of women, vaginally. It is especially convenient when the administration route is to be the same for both anti-inflammatory substance and prostaglandin or prostacyclin-type compound to combine both into a single dosage form.

The dosage regimen for the prostaglandin or prostacyclin-type compound in accord with this treatment will depend upon a variety of factors, including the type, age, weight, sex and medical condition of the mammal, the nature and dosage regimen of anti-inflammatory synthetase inhibitor being administered to the mammal, the sensitivity of the particular prostaglandin or prostacyclin-type compound to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of anti-inflammatory substance is causing undesirable gastrointestinal effects in the human or animal subject and to prescribe an effective amount of the prostaglandin or prostacyclin-type compound to reduce and then substantially to eliminate those undesirable effects.

Prostaglandin or prostacyclin-type compounds are also useful in the treatment of asthma. For example, these compounds are useful as bronchodilators or as inhibitors of mediators, such as SRS-A, and histamine which are released from cells activated by an antigen antibody complex. Thus, these compounds control spasm and facilitate breathing in conditions such as bronchial asthma, bronchitis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use the prostaglandin or prostacyclin-type compound can be combined advantageously with other asthmatic agents, such as sympathomimetics (isoproterenol, phenylephedrine, ephedrine, etc.); xanthine derivatives (theophylline and aminophylline); and corticosteroids (ACTH and prednisolone).

prostaglandin or prostacyclin-type compounds are effectively administered to human asthma patients by oral inhalation or aerosol inhalation.

For administration by the oral inhalation route with conventional nebulizers or by oxygen aerosolization it is convenient to provide the prostacyclin ingredient in dilute solution, preferably at concentrations of about 1 part of medicament to form about 100 to 200 parts by weight of total solution. Entirely conventional additives may be employed to stablize these solutions or to provide isotonic media, for example, sodium chloride, sodium citrate, citric acid, and the like can be employed.

For administration as a self-propelled dosage unit for administering the active ingredient in aerosol form suitable for inhalation therapy the composition can comprise the above ingredient suspended in an inert propellant (such as a mixture of dichloro-difluoromethane and dichloro-tetrafluoroethane) together with a co-solvent, such as ethanol, flavoring materials and stabilizers. Instead of a co-solvent there can be used a dispensing agent such as oleyl alcohol. Suitable means to employ the aerosol inhalation therapy technique are described fully in U.S. Pat. No. 2,868,691 for example.

Prostaglandins or prostacyclin-type compounds are useful in mammals, including man, as nasal decongestants and are used for this purpose in a dose range of about 10 $\mu$g. to about 10 mg. per ml. of a pharmacologically suitable liquid vehicle or as an aerosol spray, both for topical application.

Prostacyclin or prostacyclin-type compounds are also useful in treating peripheral vascular disease in humans. The term peripheral vascular disease as used herein means disease of any of the blood vessels outside of the heart, the microvasculature serving the heart and to disease of the lymph vessels, for example, frostbite, ischemic cerebrovascular disease, arteriovenous fistulas, ischemic leg ulcers, phlebitis, venous insufficiency, gangrene, hepatorenal syndrome, ductus arteriosus, nonobstructive mesenteric ischemia, artritis lymphangitis and the like. These examples are included to be illustrative and should not be construed as limiting the term peripheral vascular disease. For these conditions the prostacyclin compounds are administered orally or parentally via injection or infusion directly into a vein or artery.

The dosages of such compounds are in the range of 0.01–10 $\mu$g. administered by infusions at an hourly rate or by injection on a daily basis, i.e. 1–4 times a day, the exact dose depending on the age, weight, and condition of the patient and on the frequency and route of administration. Treatment is continued for one to five days, although three days is ordinarily sufficient to assure long-lasting therapeutic action. In the event that systemic or side effects are observed the dosage is lowered below the threshold at which such systemic or side effects are observed.

Prostacyclin or prostacyclin-type compounds are accordingly useful for treating peripheral vascular diseases in the extremities of humans who have circulatory insufficiencies in said extremities, such treatment affording relief of rest pain and induction of healing of ulcers.

For a complete discussion of the nature of and clinical manifestations of human peripheral vascular disease and the method previously known of its treatment with prostaglandins see South African Pat. No. 74/0149 referenced as Derwent Farmdoc No. 58,400V. See Elliott et al., Lancet, Jan. 18, 1975, pp. 140–142. Prostaglandins or prostacyclin-type compounds are useful in place of oxytocin to induce labor in pregnant female animals with intrauterine death of the fetus from about 20 weeks to term. For this purpose, the compound is infused intravenously at a dose of 0.01 to 50 $\mu$g. per kg. of body weight per minute until or near the termination of the second stage of labor i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

Prostaglandins or prostacyclin type compounds are further useful for controlling the reproductive cycle in menstruating female mammals, including humans. By the term menstruating female mammals is meant animals which are mature enough to menstruate, but not so old that regular menstruation has ceased. For that purpose the prostaglandin compound is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

Prostaglandin or prostacyclin-type compounds are further useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by prostaglandin compounds is also useful in operative gynecology such as D and C (Cervical Dilation and Uterine Curettage) where mechanical dilation may cause perforation of the uterus, cervical tears, or infections. It is also useful for diagnostic procedures where dilation is necessary for tissue examination. For these purposes, the prostacyclin compound is administered locally or systemically.

The prostaglandin compound, for example, is administered orally or vaginally at doses of about 5 to 50 mg. per treatment of an adult female human, with from one to five treatments per 24 hour period. Alternatively the compound is administered intramuscularly or subcutaneously at doses of about one to 25 mg. per treatment. The exact dosages for these purposes depend on the age, weight, and condition of the patient or animal.

Prostaglandins and prostacyclin-type compounds are further useful in domestic animals as abortifacients (especially for feedlot heifer), as an aid to estrus detection, and for regulation or synchronization of estrus. Domestic animals include horses, cattle, sheep, and swine. The regulation or synchronization of estrus allows for more efficient management of both conception and labor by enabling the herdsman to breed all his females in short pre-defined intervals. This synchronization results in a higher percentage of live births than the percentage achieved by natural control. The prostaglandin or prostacyclin-type compound is injected or applied in a feed at doses of 0.1–100 mg. per animal and may be combined with other agents such as steroids. For example, mares are given the prostaglandin compound 5 to 8 days after ovulation and return to estrus. Cattle are treated at regular intervals over a 3 week period to advantageously bring all into estrus at the same time.

Prostaglandin or prostacyclin-type compounds increase the flow of blood in the mammalian kidney, thereby increasing volume and electrolyte content of the urine. For that reason, these compounds are useful in managing cases of renal dysfunction, especially those involving blockage of a renal vascular bed. Illustratively, these compounds are useful to alleviate and correct cases of edema resulting, for example, from massive surface burns, and in the management of shock. For these purposes, these compounds are preferably first administered by intravenous injection at a dose in the range 10 to 1000 μg. per kg. of body weight or 0.001 to 10 μg. per kg. of body weight per minute until the desire effect is obtained. Subsequent doses are given by intravenous, intramuscular, or subcutaneous injection or infusion in the range 0.05 to 2 mg. per kg. of body weight per day.

Prostaglandin or prostacyclin-type compounds are useful for treating proliferating skin diseases of man and domesticated animals, including psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosia, premalignant sun-induced keratosis, nonmalignant keratosis, acne, and seborrheic dermatitis in humans and atopic dermatitis and mange in domesticated animals. These compounds alleviate the symptoms of these proliferative skin disease: psoriasis, for example, being alleviated when a scale-free psoriasis lesion is noticeably decreased in thickness or noticeably but incompletely cleared or completely cleared.

For those purposes, such compounds are applied topically as compositions including a suitable pharmaceutical carrier, for example as an ointment, lotion, paste, jelly, spray, or aerosol, using topical bases such as petrolatum, lanolin, polyethylene glycols, and alcohols. These compounds, as the active ingredients, constitute from about 0.1% to about 15% by weight of the composition, preferably from about 0.5% to about 2%. In addition to topical administration, injection may be employed, as intradermally, intra- or perilesionally, or subcutaneously, using appropriate sterile saline compositions.

Prostaglandin or prostacyclin-type compounds are useful as antiflammatory agents for inhibiting chronic inflammation in mammals including the swelling and other unpleasant effects thereof using methods of treatment and dosages generally in accord with U.S. Pat. No. 3,885,041, which patent is incorporated herein by reference.

Antiplatelet substances such as $PGI_2$ are known and have been used to afford relief from the aggregate condition.

$PGI_2$ is a notably unstable substance. Although effective, $PGI_2$ often affords unwanted hypotensive effects. However, there may be occasions when such a hypotensive effect is desirable, such as in the treatment of hypertension. Also the antiplatelet aggregation effect is short lived (and the hazardous condition associated with uncontrolled platelet aggregation returns quickly). The stability of $PGI_2$ as a medicine is not satisfactory because its half life at physiological pH is only about several minutes. The instability of $PGI_2$ is considered to be due to the fact that chemically the vinyl ether structure containing a double bond at $\Delta^5$ is readily hydrated to 6-oxoprostaglandin $F_{1\alpha}$ and in vivo, it is rapidly metabolized by a 15-position dehydrogenase. On the other hand, $PGI_2$ is considered to be not entirely satisfactory in its pharmacological actions because its doses required for platelet aggregation inhibiting action and antihypertensive action are almost equal to each other and its selectivity of action as a medicine is inferior. Accordingly, a great deal of efforts have been made in the art to synthesize many kinds of $PGI_2$ and remedy the aforesaid defects of $PGI_2$ (see, for example, S. M. Roberts, Chemistry, Biochemistry & Pharamcological Activity of Prostanoids, Pergamon Press, Oxford, 1979). New Synthetic Routes to Prostaglandins and Thromboxanes, Eds S. M. Roberts and F. Scheinmann, Academic Press, 1982). Additional examples of stabilized $PGI_2$ structures can be found in European patent application No. 0054795A2 at page 2, which is herein incorporated by reference.

PGI derivatives and prostacyclin derivatives are well known in the art as described above. U.S. Pat. Nos. 4,123,444 and 4,124,599 described PG derivatives namely prostacyclins. These patents describe 5 and 6 keto substituents as well as 9-deoxy-9-deoxo-9-hydroxymethyl substituents. The patents are described as having general prostaglandin activity. U.S. Pat. No. 4,145,535 relates to certain trans-4, 5-didehydro-PGI compounds which are also stated to exhibit general prostacyclin like properties. U.S. Pat. No. 4,233,121 describes certain 5-halo-6,9-oxido prostaglandin derivatives which have anticoagulant activity. European patent application No. 0054795A2/1982 discloses novel 5 or 7 monohalogenated or 5,7-dihalogenated prostacyclins useful for controlling vascular actions and inhibiting tumor matastasis.

BRIEF DESCRIPTION OF THE DRAWINGS

Chart A Structure I discloses the numbering system of the allenic prostacyclin compounds of this invention. Structure II discloses the numbering system of the prostane skeleton. Structure III discloses the numbering system for prostacyclin.

Chart B Illustrates the general reaction scheme I for the synthesis of the allenic prostacyclins.

Chart C Illustrates the general reaction scheme II for synthesis of the allenic prostacyclins.

SUMMARY OF THE INVENTION

The present invention particularly provides:
A compound of the formula:

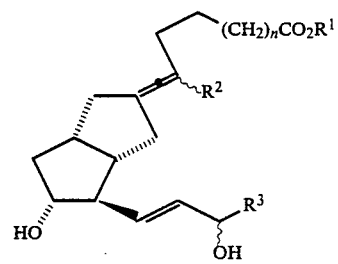

wherein:
n is 0, 1, or 2;
$R^1$ is hydrogen, lower alkyl, or a pharmaceutically acceptable cation;
$R^2$ is hydrogen, lower alkyl, cycloalkyl, heteroaryl, halogen, phenyl, alkylthio, phenylthio, alkylsulfinyl, phenylsulfinyl or trifluoromethyl;

$R^3$ is lower alkyl, cycloalkyl, phenyl, benzyl, cycloheteroalkyl, lower alkyl having one to eight carbons substituted with one or more fluorines or containing 1 or 2 unsaturated bonds; and carbon 15 may be in the R or the S configuration, or a mixture of R and S.

The allenic prostacyclins of the present invention represent novel chemical structures that are chemically stable in the dry state or in solution as a sodium, potassium or calcium salt. These allenic prostacyclins present a superior therapeutic profile when compared with prostacyclin. The allenic compounds of the present invention, unlike the prior art prostacyclin compounds, unexpectedly were found not to cause an undesirable hypotensive effect when administered Lower alkyl is a straight or a branched hydrocarbon chain having one to eight carbons. Cycloalkyl is a cyclic hydrocarbon group compound containing three to seven carbons. Cycloheteroalkyl is a cycloalkyl in which one ring carbon is replaced with one oxygen or one sulfur. Heteroaryl is an aromatic ring system having 5 or 6 ring atoms wherein one such ring atom is nitrogen, oxygen, or sulfur, and the other such ring atoms are carbons. Alkylthio is a sulfur substituted with a lower alkyl. Alkylsulfinyl is a sulfinyl function substituted with a lower alkyl. A pharmaceutically acceptable cation is cation that, when combined to form a salt with an anion such as a carboxylate function, is generally considered suitable for human consumption.

$R^1$ may be a lower alkyl, such as methyl, ethyl, propyl, butyl and the like. $R^1$ may be H or a pharmaceutically acceptable cation, such as sodium, potassium, calcium, or a quaternary alkyl ammonium ion.

$R^2$ may be a lower alkyl, such as methyl, ethyl, propyl, butyl, pentyl, hexyl, heptyl, octyl and the like. $R^2$ may a cycloalkyl, such as cyclopropyl, cyclobutyl, cyclopentyl, cyclohexyl and the like. $R^2$ may be a heteroaryl, such as pyridyl, furyl, or thienyl; a halogen such as fluorine, chlorine or bromine; phenyl; an alkylthio such as methylthio; phenylthio; an alkyl sulfinyl such as methylsulfinyl; phenylsulfinyl; or trifluoromethyl.

$R^3$ may be a cycloalkyl containing three to seven carbons, such as cyclopropyl, cyclobutyl, cyclopentyl, cyclohexyl, cycloheptyl and the like. $R^3$ may be a cycloheteroalkyl, such as tetrahydropyranyl, tetrahydrofuranyl, tetrahydrothiopyranyl and the like. $R^3$ may be lower alkyl containing 1 or 2 unsaturated bonds, that is, lower alkene or lower alkyne. $R^3$ may be lower alkene, such as ethylene, propylene, 1-butene, 2-butene, 1-pentene, 2-pentene, 3-pentene, 1-hexene, 2-hexene, 1-heptene, 2-heptene, 1-octene, 2-octene and the like. $R^2$ alkenes may be in either the cis or trans configuration. $R^3$ may be lower alkyne, such as acetylene, propyne, 1-butyne and the like, 1-pentyne and the like, 1-hexyne and the like, 1-heptyne and the like, and 1-octyne and the like, and may be optionally substituted by methyl, dimethyl or fluoro. $R^3$ may be a lower alkyl such as ethyl, propyl, butyl, pentyl, hexyl, heptyl or octyl and may be optionally substituted by fluoro. $R^3$ may also be phenyl or benzyl.

The term "carbon 15" refers to the side-chain carbon labeled as such in Chart A, structure I. To maintain consistency with usual prostanoid numbering schemes, the central allenic carbon is labeled "5a" and the term "carbon 15" is applied to the same side-chain carbon, regardless of whether n is 0, 1, or 2. Carbon 15 may have the R or S configuration or be a mixture thereof.

DESCRIPTION OF THE PREFERRED EMBODIMENTS

General Method

The allenic carbacyclins of this invention may be obtained as outlined in Scheme I or II or a modification thereof.

The starting material for Scheme I (I) is obtained as in P. A. Aristoff, J. Org. Chem, 46, 1954 (1981). $R^3$ can be adjusted as necessary (For synthesis of different $R^3$s see Prostaglandin Synthesis, J. S. Bindra and R. Bindra, Academic Press 1977, p. 462)

$PG^2$ is a suitable protecting group, e.g. ethoxyethyl, tetrahydropyranyl or trialkylsilyl.

$PG^1$ is a suitable protecting group, e.g. trialkylsilyl when $PG^2$=ethoxyethyl (EE) or tetrahydropyranyl (THP) or tert-butylmethoxyphenylsilyl when $PG^2$=trialkylsilyl.

Treatment of this bicyclic ketone(I) with an acetylide anion of the type VII (generated from the alkyne and an appropriate base such as n-butyl lithium, see, for example, E. P. Oliveto in J. Fried and J. A. Edwards. Organic Reactions in Steroid Chemistry, Vol. II, Van Nostrand Reinhold Comp., New York 1972, p. 139) provides an intermediate alkoxide which can be quenched with water to give the propargylic carbinol (II) or trapped with a suitable electrophile, say acetic anhydride, to afford for example the propargylic acetate VIII [A propargylic sulfinate would be another possibility, see, for example, H. Westmijze, I. Nap, J. Meijer, H. Kleijn and P. Vermeer, Recl. Trav. Chim. Pays-Bas, 102, 154 (1983) and references therein.] The carbinol (II) may be treated with an electrophile such as benzenesulfenyl chloride to afford the allenic sulfoxide (III) which can be converted to the allene using a base such as methyl lithium (See, V. Van Rheenen and K. P. Shephard, J. Org. Chem., 44, 1583 (1979) and G. Neef, V. Eder and A. Seeger, Tet. Letters, 21, 903 (1980)). The protecting group on the primary hydroxyl can now be removed with a suitable fluoride source such as tetra n-butyl ammonium fluoride in tetrahydrofuran or cesium fluoride in acetonitrile or diglyme, and the alcohol converted to the corresponding acid (V, R'=H) using an appropriate oxidizing agent such as Jones reagent (8.1N) chromic acid) [For relevant literature see P. Baret, E. Barreiro, A. E. Greene, J-L. Luche, M. A. Teixeira and P. Crabbe, Tetrahedron, 35, 293 (1979)].

At this point, if an ester is required, the acid may be treated with an appropriate alkylating reagent/base combination, e.g. ethyl iodide/DBU (V, R'=Et). If a methyl ester is required, the acid may be reacted with diazomethane (V, R'=CH$_3$). If an amide is required, the acid may be condensed with an appropriate amine, e.g. dimethylamine (Me$_2$NH) in the presence of a suitable dehydrating agent such as dicyclohexylcarbodiimide (V, R'=NMe$_2$) or by other well known literature procedures. The protecting group $PG^2$, say THP, may be removed upon exposure to acid. Other $PG^2$s may be removed by methods known in the literature (see Protective groups in Organic Chemistry, T. Greene, Wiley-Interscience, 1980). Thereby, VI can be obtained.

If a salt of the carboxylic acid is required, VI can be reacted with an appropriate base, e.g. sodium hydroxide potassium hydroxide, calcium oxide or barium hydroxide (VI, R'=Na, K, Ca, Ba).

The carbinol (II) can be utilized to access halogenated or trifluoromethylated allenes by procedures known in the literature (see, for example, The Chemistry of the Allenes, S. R. Landor Ed., Vol. I, Academic Press (1982)). For instance, a chloro-allene (IX, $R^2=Cl$) can be obtained by the reaction of (II) with a chlorinating agent such as thionyl chloride in an inert solvent such as ether in the presence of a base such as pyridine or triethylamine.

Alkylated allenes or sulfur containing allenes can be accessed as shown in Scheme II. The carbinol (II) can be converted to an acetate (VIII, R=Ac) or methanesulfinate (VIII, $R=CH_3SO$) as previously described.

Compounds of type VIII can be effectively converted into allenes (IX) by treatment with an appropriate organocopper reagent, e.g. dimethyl copper lithium ($Me_2CuLi$, 4 equivalents, 0° C., ether) which affords $R^2=CH_3$. (For background on organocopper reagents, see G. Posner, An Introduction to Synthesis using Organocopper Reagents, Wiley-Interscience, 1980.) Thioallenes $R^2=S(Ph)$, $SCH_3$, etc. can be accessed using VIII or another suitable intermediate using the procedure of A. J. Bridges and R. J. Ross, Tet. Letters, 24, 4797 (1983), in which a propargylic, mesylate, triflate or methanesulfinate is reacted with a organo thiocopper complex in a solvent such as methylene chloride or benzene.

The compounds of the instant invention are novel in that, compared to natural occurring $PGI_2$, they are surprisingly more stable and are active against platelet aggregation over a longer period of time.

By virtue of this anti-platelet aggregation activity the compounds of formula I are useful in treating platelet dysfunction in human and animals. A physician or veterinarian of ordinary skills could readily determine a subject who is exhibiting platelet dysfunction symptoms. Regardless of the route of administration selected, the compounds of the present invention are formulated into pharmaceutically acceptable dosage forms by conventional methods known to the pharmaceutical arts.

The compounds can be administered in such oral unit dosage forms such as tablets, capsules, pills, powders, or granules. They also may be administered rectally, vaginally in such forms as suppositories or creams; they may also be introduced in the form of eye drops, parenterally, subcutaneously, or intramuscularly, using forms known to the pharmaceutical art. In general, the preferred form of administration is orally.

An effective but non-toxic quantity of the compound is employed in treatment. The dosage regimen for preventing or treating platelet dysfunction by the compounds of this invention is selected in accordance with a variety of factors including the type, age, weight, sex, and medical condition of the mammal, the severity of the symptoms, the route of administration and the particular compound employed. An ordinarily skilled physician or veterinarian will readily determine and prescribe the effective amount of the agent to prevent or arrest the progress of the condition. In so proceeding, the physician or veterinarian could employ relatively low dosages at first, subsequently increasing the dose until a maximum response is obtained.

The acidic compounds of this invention can also be administered as pharmacologically acceptable basic salts such as sodium, potassium and calcium.

EXPERIMENTAL SECTION $^1H$ and $^{13}C$ NMR spectra were recorded on a Varian FT80 or XL200 spectrometer at 80 or 200 MHz (for $^1H$) and 50.3 MHz (for $^{13}C$) with chemical shifts reported in parts per million ($\delta$) downfield from tetramethylsilane as an internal standard. Splitting patterns are designated as s, singlet; d, doublet; t, triplet; q, quartet; and m, multiplet Infrared spectra (IR) were obtained as solution in chloroform ($CHCl_3$) and are given in $cm^{-1}$. (Only major frequencies are recorded.) Mass Spectra were run on a Kratos MS30 or MS50 at 70 eV and an ionizing current of 300 mA.

Elemental analyses were performed by the microanalytical department at G. D. Searle & Co.

EXAMPLE 1

5-Hexyn-1-ol t-butyldimethylsilyl ether (2)

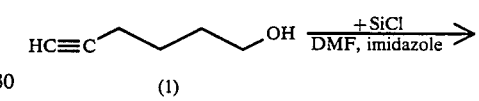

5-Hexyn-1-ol(9.8 g, 0.1 Mol) was dissolved in dry DMF (25 cm$^3$) containing Imidazole (13.6 g, 0.2 Mol) and tert-butyldimethylsilyl chloride (18.0 g, 20.1 Mol). The mixture was stirred at 25° C. under nitrogen for 10 hours and then poured into water (50 cm$^3$). The aqueous material was thoroughly extracted with hexane (4×100 cm$^3$) and the combined organic extracts washed with water (100 cm$^3$) and brine (100 cm$^3$). Evaporation of dried ($Na_2SO_4$) solvent in vacuo afforded 20.2 g of crude product, which was distilled under reduced pressure (1.5 mmHg) b.p 65° C. to afford 16.1 g of pure silyl-ether.

Analytical data

NMR ($^1H,\delta$, CDCl$_3$, 80 MHz) 3.6 (2H,t,—CH$_2$OSit-BuMe$_2$)

IR (CHCl$_3$) 3300 cm$^{-1}$ (C≡C)

Microanalysis:Found: C, 67.72, H, 11.79. Calc: C, 67.79, H, 11.30.

EXAMPLE 2

(3aβ,6aβ)-4β-[3R*-cyclopentyl-3-[(tetrahydro-2H-p-yran-2-yl)oxy]-1E-propenyl]-2-[6-[[(1,1-dimethylethyl)-dimethylsilyl]oxy]-1-hexynyl]octahydro-5α-[(tetrahydro-2H-pyran-2-yl)oxy]-2S,2α-pentalenol, acetate, and, (3aα,6aα)-4α-[3S*-cyclopentyl-3-[(tetrahydro-2H-p-yran-2-yl)oxy]-1E-propenyl]-2-[6-[[(1,1-dimethylethyl)-dimethylsilyl]oxy]-1-hexynyl]octahydro-5β-[(tetrahydro-2H-pyran-2-yl)oxy]-2R,2α-pentalenol, acetate.

(3aβ, 6aβ)-4β-[3R*-cyclopentyl-3-[(tetrahydro-2H-pyran-2-yl)oxy]-1E-propenyl]-2-[6-[[(1,1-dimethylethyl)dimethylsilyl]oxy]-1-hexynyl]octahydro-5α-[(tetrahydro-2H-pyran-2-yl)oxy]-2S,2α-pentalenol, acetate, and (3aα,6aα)-4α-[3S*-cyclopentyl-3-[(tetrahydro-2H-pyran-2-yl)oxy]-1E-propenyl]-2-[6-[[(1,1-dimethylethyl)dimethylsilyl]oxy]-1-hexynyl]octahydro-5β-[(tetrahydro-2H-pyran-2-yl)oxy]-2R,2α-pentalenol.

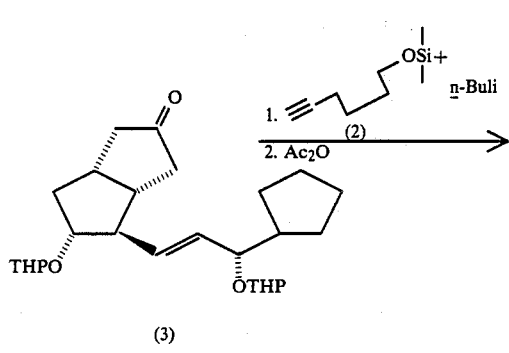

(3)

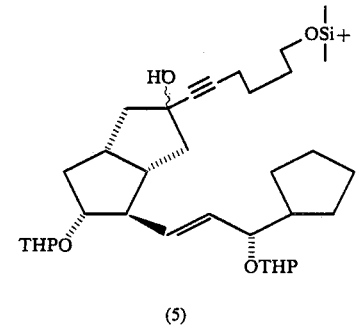

(5)

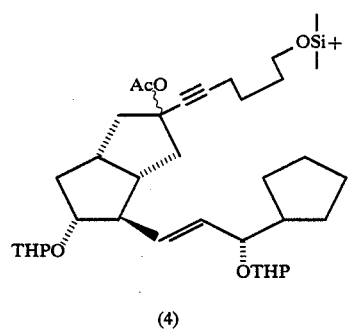

(4)

EXAMPLE 3

(3aα, 6aα)-2-[[1S*-cyclopentyl-3-[5-[6[[(1,1-dimethylethyl)-dimethylsilyl]oxy]-2S*-(phenylsulfinyl)-1-hexyliden-]octahydro-2β-[(tetrahydro-2H-pyran-2-yl)oxy]-1R, 1α-pentalenyl]-2E-propenyl]oxy]tetrahydro-2H-pyran, and, (3aα, 6aα)-2-[1S*-cyclopentyl-3-[5-[6-[[(1,1-dimethylethyl)-dimethylsilyl]oxy]-2R*-(phenylsulfinyl)-1-hexenylidene]octahydro-2β-[(tetrahydro-2H-pyran-2-yl)oxy]-1R, 1α-pentalenyl]-2E-propenyl]oxy]tetrahydro-2H-pyran.

Compound (2) (1.05 g) was dissolved in dry THF (15 cm³) and cooled to −25° C. (argon, mag. stirring). A solution of n-Butyllithium in hexane (1.63 M, 3.0 cm³) was added via syringe and the mixture stirred at −25° C. for 1 hour. At this point, Compound (3) was added as a solution in THF and the mixture stirred for 1 hour at 0° C. Ac₂O (1 cm³) was added via syringe and the mixture stirred at 0° C. for 30 minutes and then at 25° C. for 30 minutes. The mixture was partitioned between ether and sodium bicarbonate. The organic layer was separated, washed with brine and dried (Na₂SO₄). Evaporation of the volatiles in vacuo afforded 2.1g of crude product. Purification by chromatography on silica gel (Merck 60, ethylacetate/hexane 20:80) afforded 3.1g of propargylic acetates.

NMR (¹H,δ,CDCl₃, 80 MHz) 0.2 (6H,s,(CH₃)₂Si—), 0.9 (9H,s,(CH₃)C—Si—), 2.1 (3H,s,OAc) 1.25–2.5 (40H,m,cycloalkyl Hs and α chain Hs), 3.25–4.0 (8H,m,THPH's α to 0, +CH—O Hs 4.6 (2H,m,THP anomeric Hs), 5.25–5.75 (2H,m,olefinic Hs)

Ir (CHCl₃) 2210, 1745, 1250 cm⁻¹. 0.35 g of propargylic alcohols (5)

NM,R (¹H,δ,CDCl₃, 80 MHz), 0.2 (6H, s, (CH₃)₂Si—), 0.9 (9H, s, (CH₃)C—Si) 1.25–2.5 (40H, m, cycloalkyl Hs and α-chain Hs), 3.25–4.0 (8H, m, THP Hs α to 0, +CH-OHs), 4.6 (2H, m, THP anomeric Hs), 5.25–5.75 (2H, m, olefinic Hs)

The structure and names of the products are:

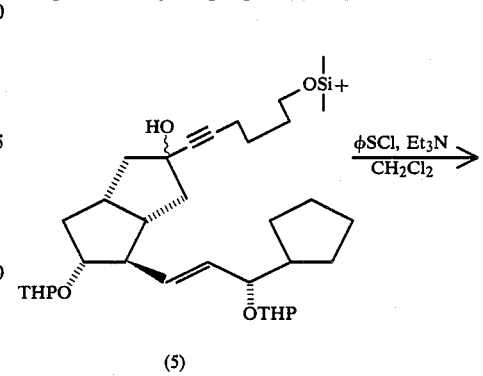

(5)

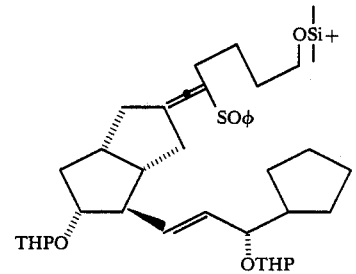

(6)

Compound (5) (0.39 g, 0.6 mMol) was dissolved in CH₂CH₂ (10 cm³) containing triethylamine (2.5 equivalents) and the mixture cooled to −70° C. A solution of benzenesulfenyl chloride (30.1 g, 1.5 equiv) was added dropwise over a period of 10 mins (mag. stirring, argon). The mixture was stirred at −70° C. for 1 hour and then warmed to −20° C. Stirring was continued at −20° C. for a further hour and the mixture was then poured into 2N NaHCO₃/CH₂Cl₂. The organic layer was separated and washed with brine; evaporation of the volatiles in vacuo afforded 410 mgs of crude product which was purified by chromatography on Merck 60 (ethyl acetate/hexane, 2:8) to afford 311 mgs of allene sulfoxides (6).

NMR (¹H,δ, CDCl₃, 80 MHz) 0.2 (6H, m, —Si(CH₃)₂), 0.9(9H,d,Sit-Bu), 1.25-2.6 (40H, m, cycloalkyl Hs and α-chain Hs), 3.3-4.0 (8, Hm, THPHs α to 0+CH—O Hs), 4.65 (2H, m, THP anomeric Hs), 5.25-5.75 (2H, m, olefinic Hs), 7.5 (5H, m. aromatic Hs)
Ir (CHCl₃) 1250, 1080, 1030, 1020 cm⁻¹

EXAMPLE 4

(3aα,6aα)-2-[[1S*-cyclopentyl-3-[5R*-[6-[[(1,1-dimethylethyl)dimethylsilyl]oxy]-1-hexenylidene]octahydro-2-[(tetrahydro-2H-pyran-2-yl)oxy]-1R,1α-pentalenyl]-2E-propenyl]oxy]-tetrahydro-2H-pyran, and, (3aα,6aα)-2-[[1S*-cyclopentyl-3-[5S*-[6-[[(1,1-dimethylethyl)dimethylsilyl]oxy]-1-hexenylidene]octahydro-2-[(tetrahydro-2H-pyran-2-yl)oxy]-1R,1α-pentalenyl]-2E-propenyl]oxy]tetrahydro-2H-pyran

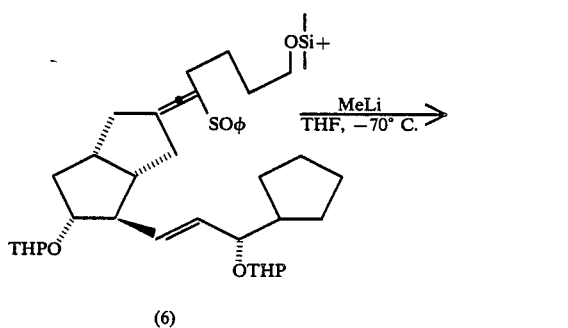

(6)

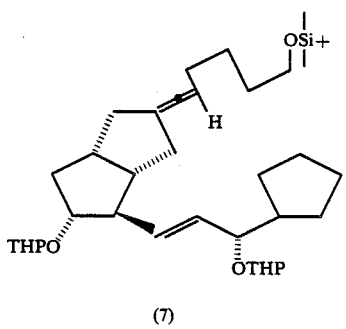

(7)

Compound (6) (0.311 g, 0.411mMol) was dissolved in dry THF (10 cm³) (−70° C., argon, stirring) and methyllithium (1.2M in Et₂O, 1.4 cm³, 4 equiv) added via a syringe. The mixture was stirred at −70° C. for 15 minutes and then quenched with ammonium chloride solution. The cold mixture was thoroughly extracted with ether and the combined organic extracts washed with brine and dried (Na₂SO₄). Evaporation of the volatiles in vacuo afforded 0.25 g of crude product. Chromatography on Merck 60 silica gel (10% ethyl acetate/hexane) afforded 170 mgs of pure allene sulfoxides 7(69%).

NMR (¹H,δ, CDCl₃, 80 MHz) 0.2 (6H, m, —Si(CH₃)₂), 0.9(9H,d,Sit-Bu) 1.25-2.6 (40H, m, cycloalkyl Hs and α-chain Hs), 3.3-4.0 (8H, m, THP Hs α to 0+CH—O Hs) 4.65 (2H, m, THP anomeric Hs), 5.05 (1H, m, allene H) 5.25-5.75 (2H, m, olefinic Hs)
Ir (CHCl₃) 1250, 1110, 1045, 1020 cm⁻¹.

EXAMPLE 5

(3aS,3aα,6aα)-6-[4α-[3R*-cyclopentyl-3-[(tetrahydro-2H-pyran-2-yl)oxy]-1E-propenyl]hexahydro-5β-[(tetrahydro-2H-pyran-2-yl)oxy]-2(1H)-pentalenylidene]-5S*-hexen-1-ol, and, (3aS,3aα,6aα)-6-[4α-[3R*-cyclopentyl-3-[(tetrahydro-2H-pyran-2-yl)oxy]-1E-propenyl]hexahydro-5β-[(tetrahydro-2H-pyran-2-yl)oxy]-2(1H)-pentalenylidene]-5R*-hexen-1-ol.

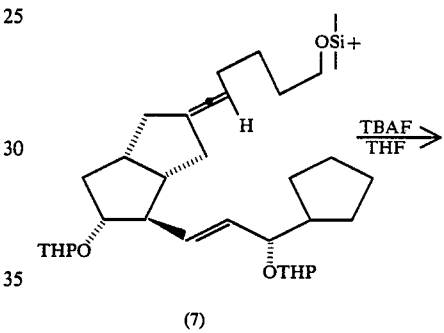

(7)

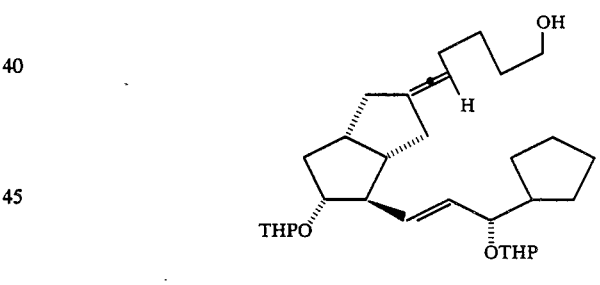

(8)

Compound (7) (0.35 g, 0.59 mMol) was dissolved in anhydrous THF (10 cm³) and a solution of tetrabutylammonium fluoride in THF (1M, 2cm³, xs) was added via syringe. The mixture was stirred at 25° C. for 10 hours (argon) and then partitioned between ether and 2N NaHCO₃. The organic layer was separated and the aqueous layer thoroughly extracted with ether. The combined organic extracts were washed with brine, dried (Na₂SO₄) and evaporated in vacuo. The crude product was purified by chromatography on silica gel (Merck 60, EA/hexane 35:65) to afford 0.17 g of alcohol.

NMR (¹H, δ, CDCl₃, 200 MHz) 1.2-2.65 (40 H, m cycloalkyl Hs and α-chain Hs), 3.3-4.0 (8H, m, THP Hs α to 0+CH—O Hs), 4.65 (2H, m, THP anomeric Hs), 5.1 (1H, m, allene H) 5.25-5.75 (2H, m, olefinic Hs)
Ir (CHCl₃) 3450-3500 cm⁻¹

EXAMPLE 6 methyl
(3aS,3aα,6aα)-6-[4α-[3R*-cyclopentyl-3-[(tetrahydro-2H-pyran-2-yl)oxy]-1E-propenyl]hexahydro-5β-[(tetrahydro-2H-pyran-2-yl)oxy]-2(1H)-pentalenylidene]-5S*-hexenoate, and, methyl
(3aS,3aα,6aα)-6-[4α-[3S*-cyclopentyl-3-[(tetrahydro-2H-pyran-2-yl)oxy]-1E-propenyl]hexahydro-5β-[(tetrahydro-2H-pyran-2-yl)oxy]-2(1H)-pentalenylidene]-5R*-hexenoate.

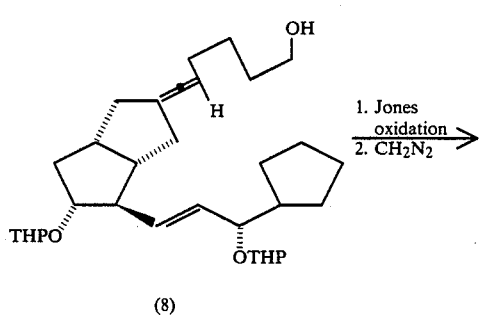

(8)

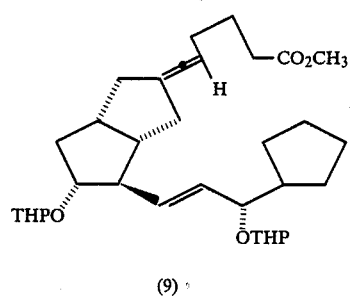

(9)

Compound (8) (0.12 g, 0.2 mMol) was dissolved in distilled (acetone (10 cm³) at −25° C. Jones reagent (0.21 cm³) was added dropwise via a syringe. The mixture was stirred at −20° C. for 2 hours and then quenched with isopropanol (1 cm³). The mixture was partitioned between EtOAc and brine; the organic layer was separated and the aqueous layer thoroughly extracted with more EtOAc. The combined organic extracts were dried ($Na_2SO_4$) and evaporated in vacuo. The crude gum thus obtained was treated with excess diazomethane in ether and evaporated under nitrogen. The product was purified by chromatography on Merck silica gel 60 (hexane/EA 9:1) to afford 75 mgs of ester.

NMR ($^1$H, δ, $CDCl_3$, 200 MHz) 1.2–2.65 (40 H, m, cycloalkyl Hs and α-chain Hs), 3.3–4.0 (6H, m, THP Hs α to 0+CH—O Hs) 3.7 (3H, s, $CO_2CH_3$) 4.65 (2H, m, THP anomeric Hs), 5.1 (1H, m, allene H), 5.25–5.75 (2H, m, olefinic Hs)

Ir ($CHCl_3$) 1730 cm$^{-1}$

EXAMPLE 7 methyl
(3aS,3aα,6aα)-6-[4α-(3R*-cyclopentyl-3-hydroxy-1E-propenyl)hexahydro-5β-hydroxy-2(1H)-pentalenylidene]-5S*-hexenoate, and, methyl
(3aS,3aα,6aα)-6-[4α-(3R*-cyclopentyl-3-hydroxy-1E-propenyl)hexahydro-5α-hydroxy-2(1H)-pentalenylidene]-5R*-hexenoate

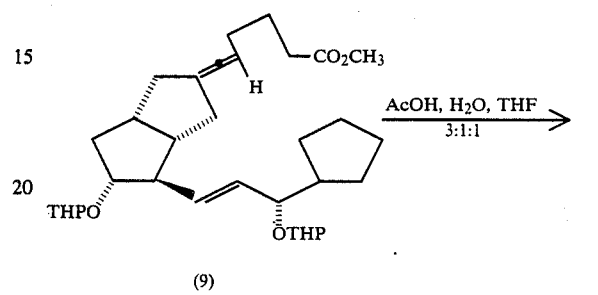

(9)

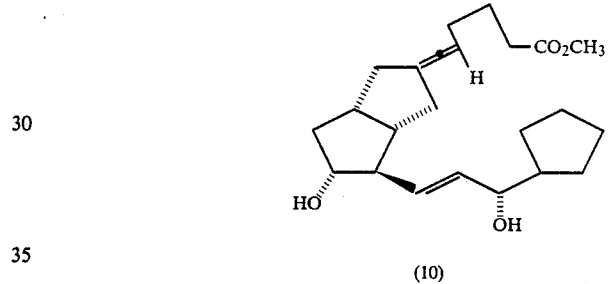

(10)

Compound (9) (75 mg) was dissolved in a mixture of acetic acid, THF and water (5 cm³, 3:1:1) and stirred under argon at 25° C. for 24 hrs. At this point, the reaction was neutralized with solid $K_2CO_3$ and partitioned between EtOAc and water. The organic layer was separated and the aqueous layer thoroughly extracted with more EtOAc. The combined organic extracts were dried ($Na_2SO_4$) and evaporated in vacuo to afford 60 mgs of crude product. Careful chromatography on silica gel (Merck 60, EA/hexane 55:45) afforded 52 mgs of α-H allene and 4 mgs of β-H allene.

NMR ($^1$H, δ, $CDCl_3$, 200 MHz) 1.2–2.6 (24H, m, cycloalkyl and α-chain H's), 2.9 (2H, broad, OH), 3.65 (3H, s, $CO_2CH_3$), 3.65–3.85 (2H, m, CH—0 Hs), 5.1 (1H, m, allene H), 5.5 (2H, m, olefinic Hs) ($^{13}$C, δ, $CDCl_3$ 50.3 MHz)

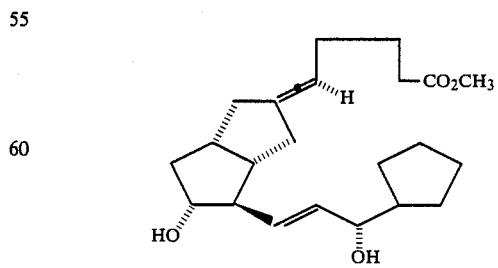

IR ($CHCl_3$) 3500 (broad), 1730 cm$^{-1}$

Microanalysis: $C_{23}H_{34}O_4$ requires C:73.76, H:9.15; Found C:73.4, H:9.03.

EXAMPLE 8

(3aS,3aα,6aα)-6-[4α-(3R*-cyclopentyl-3-hydroxy-1E-propenyl)hexahydro-5β-hydroxy-2(1H)-pentalenylidene]-(5S*)-hexenoic acid sodium salt

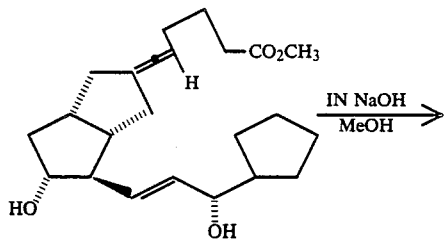

(10)

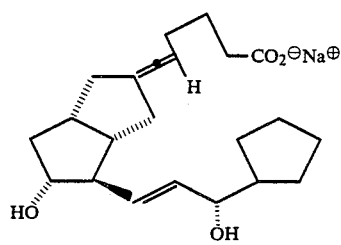

(11)

Compound (10) (40 mgs) was dissolved in methanol (0.5 cm³) and 1.1 equivalents of a 1N solution of sodium hydroxide in water were added via syringe. The mixture was stirred under argon at 25° C. for 10 hours and then evaporated in vacuo to afford 42 mgs of sodium salt (11).

EXAMPLE 9

(3aα, 6aα)-2-[[1S*-cyclopentyl-3-[5-[6-[[(1,1-dimethylethyl)dimethylsilyl]oxy]-2R*-methyl-1-hexenylidene]octahydro-2β-[(tetrahydro-2H-pyran-2-yl)oxy]-1R,1α-pentalenyl]-2E-propenyl]oxy]tetrahydro-2H-pyran, and (3aα,6aα)-2-[[1S*-cyclopentyl-3-[5-[6-[[(1,1-dimethylethyl)dimethylsilyl]oxy]-2S*-methyl-1-hexenylidene]octahydro-2β[(tetrahydro-2H-pyran-2-yl)oxy]-1R,1α-pentalenyl]-2E-propenyl]oxy]tetrahydro-2H-pyran

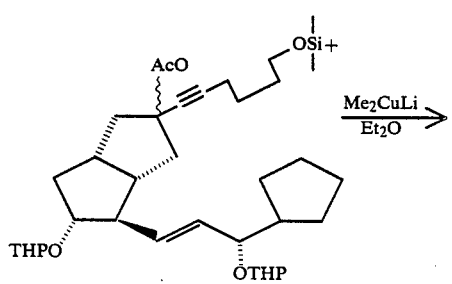

(4)

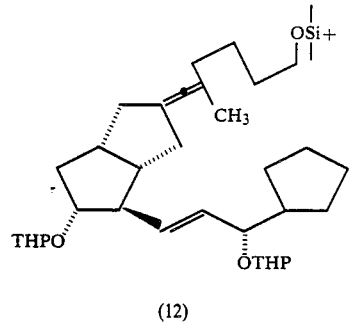

(12)

Compound (4) (0.634 g, 0.92 mMol) in dry Et₂O (2 cm³) was added via syringe to a solution of lithium dimethylcuprate (4 equivalents) in ether at −20° C. (Mag. stirring, argon). The reaction mixture was stirred at 0.5° C. for 2 hours and then quenched with NH₄Cl solution. The mixture was thoroughly extracted with ether and the combined extracts were washed with water, brine and then dried (Na₂SO₄). Evaporation of the volatiles in vacuo afforded 0.61 g of crude product which was purified by chromatography on silica gel (Merck 60, 10% EA/hexane) to afford 0.578 g of allenes (97%)

NMR (¹H, δ, CDCl₃, 80 MHz) 0.2 (6H, m, —Si(CH₃)₂), 0.9(9H,d,Sit-Bu)1.25-2.6 (40H, m, cycloalkyl Hs and α-chain Hs), 1.85 (3H, s, allenic CH₃), 3.3–4.0 (8H, m, THPHs α to 0+<u>CH</u>—0 Hs), 4.65 (2H, m, THP anomeric Hs), 5.25–5.75 (2H, m, olefinic Hs)

(¹³C, δCDCl₃, 50.3 MHz)

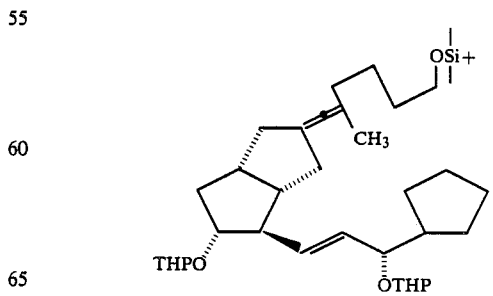

Ir (CHCl₃) 1250, 1110, 1072, 1030, 1020 cm⁻¹

EXAMPLE 10

(3aS,3aα,6aα)-6-[4α-[3R*-cyclopentyl-3-[(tetrahydro-2H-pyran-2-yl)oxy]-1E-propenyl]hexahydro-5β-[tetrahydro-2H-pyran-2-yl)oxy]-2(1H)-pentalenylidene]-5S*-methyl-5-hexen-1-ol, and, (3aS,3aα,6aα)-6-[4α-[3R*-cyclopentyl-3-[(tetrahydro-2H-pyran-2-yl)oxy]-1E-propenyl]hexahydro-5β[(tetrahydro-2H-pyran-2-yl)oxy]-2(1H)-pentalenylidene]-5R*-mehtyl-5-hexen-1-ol.

EXAMPLE 11 methyl (3aS,3aα,6aα)-6-[4α-[3R*-cyclopentyl-3-[(tetrahydro-2H-pyran-2-yl)oxy]-1E-propenyl]hexahydro-5β-[(tetrahydro-2H-pyran-2-yl)oxy]-2(1H)-pentalenylidene]-5S*-methyl-5-hexenoate, and, methyl (3aS,3aα,6aα)-6-[4α-[3R*-cyclopentyl-3-[(tetrahydro-2H-pyran-2-yl)oxy]-1E-propenyl]hexahydro-5-β-[(tetrahydro-2H-pyran-2-yl)oxy]-2(1H)-pentalenylidene]-5R*-methyl-5-hexenoate.

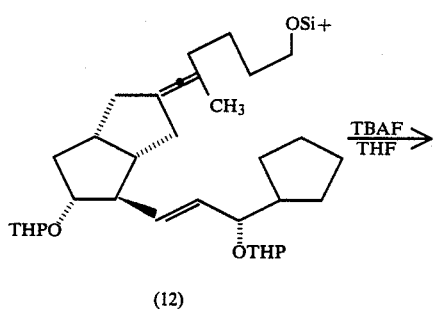

(12)

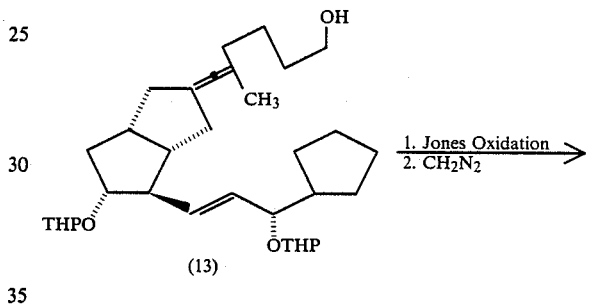

(13)

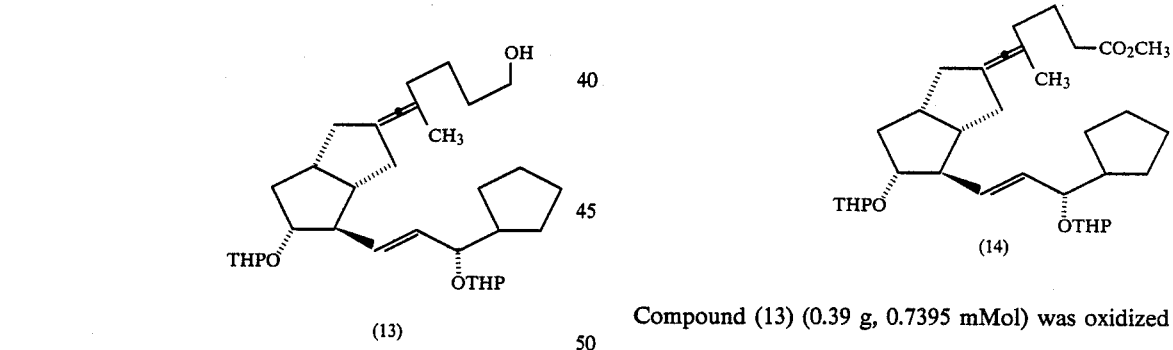

(13)

(14)

Compound (12) (0.538 g, 0.8 mMol) was treated with an excess of n-Bu₄NF (1M in THF) as in Example 5. Chromatography on silica gel (Merck 60, 25% EA/hexane) afforded 0.48 g of alcohol.

NMR ($^1$H, δ, CDCl$_3$, 80MHz) 1.25-2.6 (40 H, m, cycloalkyl Hs and α-chain Hs) 1.65 (3H, s, allenic CH$_3$), 3.3-4.0(8H, m, THP Hs α to O+CH—O Hs), 4.65 (2H, m, THP anomeric Hs), 5.25-5.75 (2H, m, olefinic Hs)

Ir (CHCl$_3$) 3500-3600 cm$^{-1}$ (ν-OH)

Compound (13) (0.39 g, 0.7395 mMol) was oxidized with Jones reagent in acetone at −20° C. as in Example 6. After treatment of the crude acid with CH$_2$N$_2$, the residue was purified by chromatography on silica gel (Merck 60, hexane/10% EA) to afford 280 mgs of ester.

NMR ($^1$H, δ, CDCl$_3$, 80 MHz) mixture of allene isomers 1.2-2.65 (40 H, m, cycloalkyl Hs and α-chain Hs), 1.65 and 1.70 (3H, 2 singlets, allene methyls), 3.3-4.0 (SH, m, THPHs α to O+CH—O Hs), 3.65 and 3.70 (3H, two singlets, CO$_2$CH$_3$) 4.65 (2H, m, THP anomeric Hs), 5.25-5.75 (2H, m, olefinic Hs).

Ir (CHCl$_3$) 1730 cm$^{-1}$

EXAMPLE 12 methyl
(3aS,3aα,6aα)-6-[4α-(3R*-cyclopentyl-3-hydroxy-1E-propenyl)hexahydro-5β-hydroxy-2(1H)-pentalenylidene-5S*-methyl-5-hexenoate, and, methyl
(3aS,3aα,6aα)-6-[4α-(3R*-cyclopentyl-3-hydroxy-1E-propenyl)hexahydro-5β-hydroxy-2(1H)-pentalenylidene]-5R*-methyl-5-hexenoate

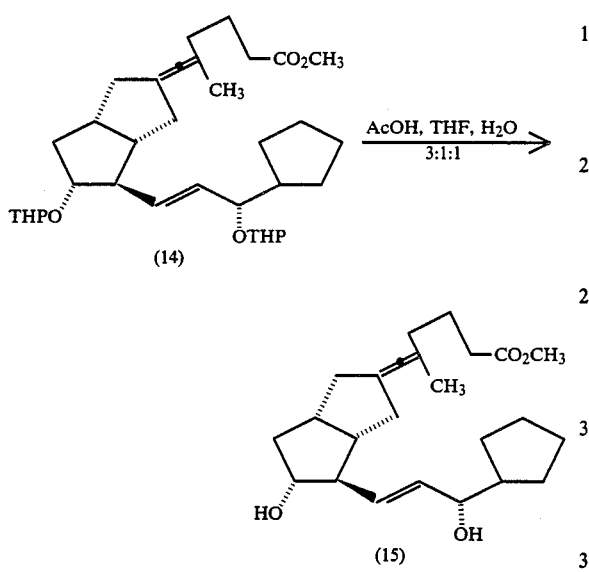

Compound (14) (0.22 g, 0.39 mMol) was treated with AcOH/THF/H₂O (15 cm³, 3:1:1) as in Example VIII. After chromatography on Merck 60 (EA/hexane 6:4) 100 mgs of β-methyl allene was obtained plus 15 mgs of α-methyl allene (slightly higher Rf) (71%).

NMR (¹H, δ, CDCl₃, 80 MHz) 1.2–2.6 (24H, m, cycloalkyl and α-chain Hs), 1.65 (3H, s, allene CH₃), 3.65 (3H, s, CO₂CH₃), 3.65–3.85 (2H, m, C$\underline{H}$—O Hs), 5.5 (2H, m, olefinic Hs), 1.2–2.6 (24H, m, cycloalkyl and α-chain Hs), 1.7 (3H, s, allene CH₃), 3.70 (3H, s, CO₂CH₃), 3.65–3.85 (2H, m, C$\underline{H}$—O Hs), 5.5 (2H, m, olefinic Hs) (¹³C, δ, CDCl₃, 50.3 MHz)

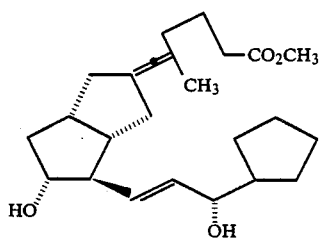

Ir (CHCl₃) 3500–3400, 1730 cm⁻¹
High Resolution M.S. M+—H₂O, Found for C₂₄H₃₄O₃ 370.2501; Deviation from calculated M+—H₂O=−2.0 ppm. M+—(H₂O)₂, Found for C₂₄H₃₂O₂ 352.2398; Deviation from calculated M+—(H₂O)₂=−1.4 ppm.

EXMAPLE 13

(3aS,3aα,6aα)-6-[4α-(3R*-cyclopentyl-3-hydroxy-1E-propenyl)hexahydro-5β-hydroxy-2(1H)-pentalenylidene]-5R*-methyl-5-hexenoic acid, sodium salt

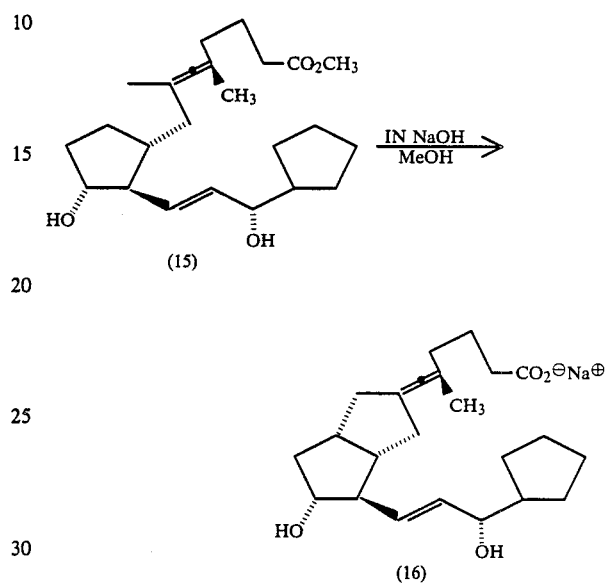

Compound (15) (0.115 g, 0.28 mMol) was saponified in the manner described previously in Example 8. Thus obtained were 120 mgs of a cream-white amorphous solid compound (16).

EXMAPLE 14

(3aα,6aα)-2-[3-[5-[2R*-chloro-6-[[(1,1-dimethylethyl)dimethylsilyl)oxy]-1-hexenylidene]-1R,1α-[3S*-cyclopentyl-3-[(tetrahydro-2H-pyran-2-yl)oxy]-1E-propenyl-]octahydro-2β-pentalenyl]oxy]tetrahydro-2H-pyran,
and, (3aα,6aα)-2-[3-[5-[2S*-chloro-6-[[(1,1-dimethylethyl)dimethylsilyl]oxy]-1-hexenylidene]-1R,1-[3S*-cyclopentyl-3[(tetrahydro-2H-pyran-2-yl)oxy]-1E-propenyl-]octahydro-2αpentalenyl]oxy]tetrahydro-2H-pyran

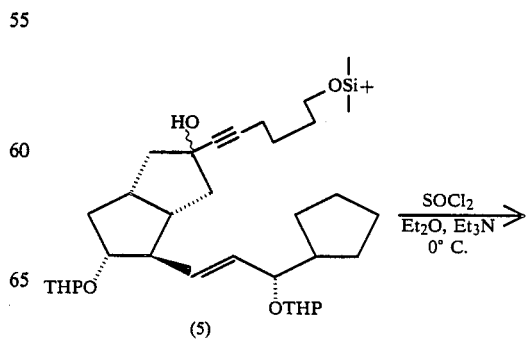

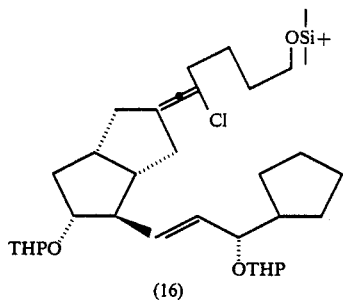

(16)

Compound (5) (0.39 g, 0.6 mMol) was dissolved in dry ether (10 cm³) containing triethylamine (1.5 equivalents) and the mixture cooled to −20° C. Thionyl chloride (1.0 equivalents) was added via a syringe and the mixture stirred at 0° C. until all starting material had been consumed. The mixture was partitioned between sodium bicarbonate and ether. The organic layer was separated, dried (Na₂SO₄) and evaporated in vacuo to afford the crude product which could be purified by chromatography on silica gel (Merck 60).

EXMAPLE 15

(3aα,6aα)-2-[[1S*-cyclopentyl-3-[5-[6-[[(1,1-dimethylethyl)dimethylsilyl]oxy]-2-(phenylthio)-1-hexenylidene]octahydro-2-β[(tetrahydro-2H-pyran-2-yl)oxy]-1R,1α-pentalenyl]-2E-propenyl]oxy]tetrahydro-2H-pyran

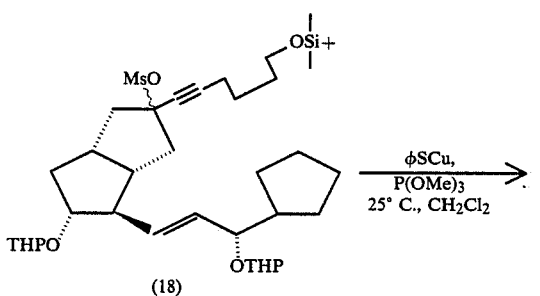

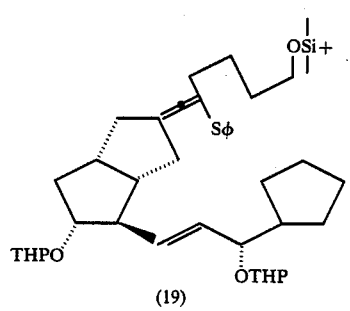

(19)

Mesylate (18) (prepared in situ by the Method of Crossland and Servis, J. Org. Chem., 35, 3195 (1970) was treated as a solution in CH₂Cl₂ at 0° C. with one equivalent of phenylthiocopper-trimethylphosphite complex. The mixture was stirred at room temperature overnight and then partitioned between ether and cold dilute hydrochloric acid. The suspension was filtered under vacuum and the organic layer washed with water and brine and then dried (Na₂SO₄). Chromatography of the crude product provided pure (19).

BIOLOGICAL TESTING

The Inhibition of ADP-Induced Platelet Aggregation

The procedure for testing platelet anti-aggregatory activity in vitro is the following one described by E. R. Waskawic. Aggregation was determined with a Payton Dual Channel Aggregation module. A Riken-Denshi recorder was used for recording the aggregation curves.

Citrated whole blood (1 part 3.8% sodium citrate and 9 parts blood) was centrifuged to obtain platelet rich plasma (PRP) (700 RPM for 11 mins.) in an IE centrifuge (Model PR 6000). After the PRP fraction was removed, the remainder was spun at 900 ×g for 15 mins. to obtain platelet poor plasma (PPP) (1800 RPM in IEC PR 6000). The number of platelets per ml PRP is determined by counting a 5 µl aliquot of PRP in a Coutter ZBI counter and channelyzer Model C-1000.

PRP is diluted with PPP 1:2 to obtain a count of approx. 25000 on the screen or $10^9$ platelets/ml PRP to evaluate the anti-aggregating agent. The module was standardized with an aliquot of PPP and that of diluted PRP.

The aggregating agent used is ADP prepared as follows:

4.7 mgs ADP (MW 427) in 10 ml saline yields a 10 µL PRP, of ADP disodium (MW=473).

| Vol. of stock (ml) | Volume of saline (ml) | [f] cuvette (µM) |
|---|---|---|
| 1.6 | 0.4 | 8 |
| 1.2 | 0.8 | 6 |
| 0.8 | 1.2 | 4 |
| 0.4 | 1.6 | 2 |
| 0.2 | 1.8 | 1 |

[f] = final concentration

Prostacyclin is used as the standard of antiaggregatory activity for determining the potency of compounds tested. A $10^2$M solution (to give a starting concentration of $10^{-4}$M when 4 µL is added to 400 µL PRP) is diluted serially to obtain solutions with final concentrations of $10^{-6}$, $10^{-7}$, $10^{-8}$, $10^{-9}$ M.

Compounds to be screened are dissolved in absolute ethanol, saline or water to achieve a $10^{-2}$M solution if 4 µL added to PRP giving a [f] in the cuvette equal to $10^{-4}$M. Serial dilutions in saline give $10^{-5}$, $10^{-6}$ and $10^{-7}$M.

1. Determine the dose of ADP which on a standard curve would be on the linear portion and allow reversal of the aggregation curve.

2. Determine the PGI₂ standard curve of percentage inhibition of aggregation. Use saline in control cuvette to compare the extent of inhibition by PGI₂ as represented by the depth of the aggregation curve. Allow the PRP to preincubate for approximately one minute prior to the addition of prostacyclin and another minute with PGI₂ prior to the addition of ADP.

% Inhibition of control = 100.00 −

$$\left( \frac{\text{experimental parameter}}{\text{control parameter}} \times 100 \right)$$

The % inhibition is plotted against prostacyclin dose on semilog paper. The $IC_{50}$ value is equal to the $PGI_2$ dose effecting 50% inhibition of the control response.

3. The test compound is added to PRP and preincubated for 1 minute prior to ADP administration. If the compound has an $IC_{50}$ less than $10^{-4}M$, it is considered to be active.

Hypotensive Activity in the Hexamethonium Treated Rat

Animals are anesthetized with barbital (100 mg kg) and pentobarbital (25 mg/kg). A tracheotomy tube is inserted and animals are allowed to breathe 100% $O_2$ spontaneously. Jugular and carotid cannulae are implanted (for drug administration and pressure measurement, respectively). Animals are maintained at 37° C. body temperature. Rats are then dosed with 1 mg/kg hexamethonium, i.v. bolus. Steady-state levels are allowed to be reached in 5 min. and animals are dosed with drug. All compounds are dissolved in either dimethyl sulfoxide or aqueous ethanol or glycine buffer (pH ~10), and in a volume of 1 ml/kg. Approximate $ED_{50}$ doses are administered and changes in mean arterial pressure are recorded every 30 sec. for 5 min. Surprisingly, the tested compounds, while active in the inhibition of ADP induced platelet aggregation, did not exhibit the hypotensive effect exhibited by the prostacyclins.

| BIOLOGICAL TESTING OF SELECT EXAMPLES | | |
|---|---|---|
| Compound | In Vitro Inhibition of ADP Induced Platelet Aggregation | Hypotensive Effect |
| Example 7 | $1 \times 10^{-6}$ M | None up to 100 mg/kg |
| Example 8 | $4 \times 10^{-6}$ M | None up to 100 mg/kg |
| Example 12 | $1.3 \times 10^{-5}$ M | None up to 100 mg/kg |
| Example 12 | $1.0 \times 10^{-6}$ M | None up to 100 mg/kg |

-continued

BIOLOGICAL TESTING OF SELECT EXAMPLES

| Compound | In Vitro Inhibition of ADP Induced Platelet Aggregation | | Hypotensive Effect |
|---|---|---|---|
| Example 13 |  | $2.1 \times 10^{-7}$ M | None up to 100 mg/kg |
| Example 13 |  | $1 \times 10^{-5}$ M | None up to 100 mg/kg |

What we claim is:

1. A compound of the formula:

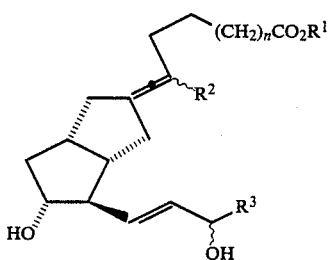

wherein:

n is 0, 1, or 2;

$R^1$ is selected from hydrogen, lower alkyl, and a pharmaceutically acceptable cation;

$R^2$ is selected from hydrogen, lower alkyl, cycloalkyl, halogen, phenyl, alkylthio, phenylthio, alkylsulfinyl having a straight or branched hydrocarbon chain of one to eight carbons, phenylsulfinyl, trifluoromethyl and heteroaryl provided by an aromatic ring system having 5 or 6 ring atoms wherein one such ring atom is nitrogen, oxygen, or sulfur, and the other such ring atoms are carbons, $R^3$ is selected from lower alkyl, cycloalkyl, phenyl, benzyl, cycloheteroalkyl provided by cycloalkyl in which one ring carbon is replaced with one oxygen or one sulfur, and lower alkyl having one to eight carbons substituted with one or more fluorines or containing 1 or 2 unsaturated bonds; and carbon 15 may be in the R or the S configuration, or a mixture of R and S.

2. A compound according to claim 1 with the formula:

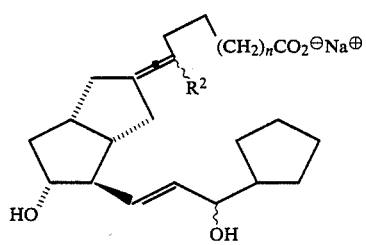

wherein: $R^2$ is selected from hydrogen, lower alkyl having one to six carbons, cycloalkyl having three to seven carbons, halogen, phenyl, alkylthio, phenylthio, alkylsulfinyl having a straight or branched hydrocarbon chain of one to eight carbons, phenylsulfinyl, trifluoromethyl and heteroaryl provided by an aromatic ring system having 5 or 6 ring atoms wherein one such ring atom is nitrogen, oxygen, or sulfur, and the other such ring atoms are carbons.

3. A compound according to claim 1 with the formula:

wherein: $R^2$ is selected from hydrogen, lower alkyl having one to six carbons, cycloalkyl having three to seven carbons, halogen, phenyl, alkylthio, phenylthio, alkylsulfinyl having a straight or branched hydrocarbon chain of one to eight carbons, phenylsulfinyl, trifluoromethyl and heteroaryl provided by an aromatic ring system having 5 or 6 ring atoms wherein one such ring atom is nitrogen, oxygen, or sulfur, and the other such ring atoms are carbons.

4. A compound according to claim 2 comprising: methyl (3aS,3aα,6aα)-6-[4α-(3R*-cyclopentyl-3-hydroxy-1E-propenyl)hexahydro-5β-hydroxy-2(1H)-pentalenylidene]-5S*-hexenoate.

5. A compound according to claim 2 comprising: methyl (3aS, 3aα,6aα)-6-[4α-(3R*-cyclopentyl-3-hydroxy-1E-propenyl)hexahydro-5β-hydroxy-2(1H)pentalenylidene]-5R*-hexenoate.

6. A compound according to claim 2 comprising: (3aS,3aα,6aα)-6-[4α-(3R*-cyclopentyl-3-hydroxy-1E-propenyl)hexahydro-5β-hydroxy-2(1H)-pentalenylidene]-5S*)-hexenoic acid sodium salt.

7. A compound according to claim 3 comprising: methyl (3aS,3aα,6aα)-6-[4α-(3R*-cyclopentyl-3-hydroxy-1E-propenyl)hexahydro-5β-hydroxy-2(1H)-pentalenylidene-5S*-methyl-5-hexenoate.

8. A compound according to claim 3 comprising: methyl (3aS,3aα,6aα)-6-[4α-(3R*-cyclopentyl-3-hydroxy-1E-propenyl)hexahydro-5β-hydroxy-2(1H)-pentalenylidene]-5R*-methyl-5-hexenoate.

9. A compound according to claim 3 comprising: (3aS,3aα,6aα)-6-[4α-(3R*-cyclopentyl-3-hydroxy-1E-propenyl)hexahydro-5β-hydroxy-2(1H)-pentalenylidene]-5R*-methyl-5-hexenoic acid, sodium salt.

* * * * *